(12) United States Patent
Magnusson et al.

(10) Patent No.: US 6,932,799 B2
(45) Date of Patent: Aug. 23, 2005

(54) ABSORBENT PRODUCT WITH DOUBLE BARRIERS AND SINGLE ELASTIC SYSTEM

(75) Inventors: Ing-Britt Magnusson, Mölnlycke (SE); Ann Samuelsson, Lindome (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/981,894

(22) Filed: Oct. 19, 2001

(65) Prior Publication Data

US 2002/0055727 A1 May 9, 2002

Related U.S. Application Data

(60) Provisional application No. 60/241,331, filed on Oct. 19, 2000.

(51) Int. Cl.[7] ............................................. A61F 13/15

(52) U.S. Cl. ........................ 604/385.04; 604/385.26; 604/385.28

(58) Field of Search ...................... 604/385.24–385.28, 604/385.04, 385.01

(56) References Cited

U.S. PATENT DOCUMENTS

| | | | |
|---|---|---|---|
| 4,695,278 A | | 9/1987 | Lawson |
| 5,607,416 A | * | 3/1997 | Yamamoto et al. ......... 604/397 |
| 5,672,166 A | | 9/1997 | Vandemoortele |
| 6,186,996 B1 | * | 2/2001 | Martin ................. 604/385.19 |
| 6,706,029 B1 | * | 3/2004 | Suzuki et al. .......... 604/385.28 |

FOREIGN PATENT DOCUMENTS

WO    WO 96/26698    9/1996

* cited by examiner

Primary Examiner—Larry I. Schwartz
Assistant Examiner—C Lynne Anderson
(74) Attorney, Agent, or Firm—Young & Thompson

(57) ABSTRACT

The invention relates to an absorbent product having a longitudinal direction and a transverse direction and comprising a front and a rear end portion (8, 10), an intermediate crotch portion (12), edges extending in the longitudinal direction and in the transverse direction, an upper, liquid-permeable surface layer (2), a lower, liquid-impermeable surface layer (4), an absorbent body (6) arranged between the surface layers (2, 4) and comprising edges in the longitudinal direction and in the transverse direction, liquid barriers (5) extending in the longitudinal direction arranged essentially parallel to those edges of the product running in the longitudinal direction, the liquid barriers (5) each having a free edge (7), side flaps (3) extending in the longitudinal direction outside the liquid barriers (5) and comprising parts of at least one of the surface layers (2, 4), and elastic elements (11; 14; 30) extending in the longitudinal direction and fastened to the liquid barriers (5) or to the side flaps (3), the liquid-permeable surface layer (2) extending in the longitudinal direction of the product at least between the liquid barriers (5). The liquid barriers (5) are, at least in the crotch portion (12) of the product, in the region between their attachment (9) to the absorbent product and their free edge (7), fixed to the adjacent side flap (3) outside the edges of the absorbent body (6), as a result of which the product has double raised leakage barriers arranged along the edges extending in the longitudinal direction.

16 Claims, 7 Drawing Sheets

ABSORBENT PRODUCT WITH DOUBLE BARRIERS AND SINGLE ELASTIC SYSTEM

This application claims benefit of provisional application No. 60/241,331, filed Oct. 19, 2000.

TECHNICAL FIELD

The present invention relates to an absorbent product, such as a nappy, an incontinence pad, a sanitary towel or the like, with a longitudinal direction and a transverse direction and comprising a front and a rear end portion, an intermediate crotch portion, edges in the longitudinal direction and in the transverse direction, an upper, liquid-permeable surface layer, a lower, liquid-impermeable surface layer, an absorbent body having edges in the longitudinal direction and in the transverse direction, liquid barriers extending in the longitudinal direction arranged essentially parallel to those edges of the product running in the longitudinal direction, each liquid barrier having a free edge, side flaps extending in the longitudinal direction outside the liquid barriers and comprising parts of at least one of the surface layers, and elastic means extending in the longitudinal direction and fastened to the liquid barriers or to the side flaps, the liquid-permeable surface layer extending at least all the way between the liquid barriers.

BACKGROUND ART

During the use of absorbent products such as nappies, sanitary towels or incontinence pads, it is frequently the case that various sorts of bodily discharges such as urine, loose stools, menstrual fluid or other bodily fluids which come into contact with that surface of the product which faces the wearer are not directly able to penetrate through the liquid-permeable surface layer of the product and into the absorbent body of the product. There is then a risk that discharged liquid will begin to move on top of the liquid-permeable surface layer and may then run out past the edges of the product. The liquid movements can take place in any direction on top of the liquid-permeable surface layer. Liquid movements in the transverse direction of the product are particularly worrying because only a relatively small liquid movement in the transverse direction involves the liquid running outside one of the long sides of the product with the result that articles of clothing, bedclothes, seat cushions and other surrounding articles are easily soiled by the discharged liquid.

Many different attempts at improvements have been made in order to eliminate this problem. It may be mentioned, for example, that the liquid-permeable surface layers have been improved considerably with regard to their capacity for allowing various types of bodily fluid to pass through quickly and thus for preventing the liquid having time to move any further on top of the surface before penetration through the surface layer takes place. The most common attempts at preventing bodily fluid running outside the long sides of the absorbent product have consisted in trying in different ways to create various forms of barrier in association with the longitudinal edges of the product in order to prevent the running liquid from passing the longitudinal edges of the product and ending up outside the product and causing leakage. Various types of barrier solution have been described.

Absorbent products having side flaps with a barrier function are described in, for example, patents EP 0,091,412, U.S. Pat. Nos. 3,860,003, 4,579,556 and 5,032,121. These patents describe absorbent products with side flaps which consist of the two covering layers of the product together with pretensioned elastic systems arranged between the covering layers. When these pretensioned elastic systems are contracted, this means that the materials in the side flaps are also contracted and are thus brought into an upwardly directed configuration in relation to the plane of the respective covering layer. In their raised configuration, the raised side flaps constitute barriers which seal effectively against the thighs/groins of the wearer.

International patent application WO 98/08474 describes another form of absorbent product with elasticated side flaps. The elasticated side flaps according to WO 98/08474 are folded in over the liquid-permeable covering layer of the product and are fixed to the liquid-permeable covering layer. The result is an absorbent product with upwardly directed barriers which are inclined in towards the longitudinal symmetry line of the product.

U.S. Pat. No. 4,904,251 describes an absorbent product with upwardly directed barriers extending in the longitudinal direction of the product between the longitudinal edges of the absorption body and the longitudinal outer edges of the side flaps. The upwardly directed configuration is brought about for this type of barrier also by pretensioned elastic threads, bands or the like being contracted together with the barrier materials.

Absorbent products containing double elasticated barrier systems are described in U.S. Pat. No. 4,695,278. This patent describes absorbent products comprising both elasticated inner barriers and elasticated side flaps. The inner barriers extend in the longitudinal direction of the product and adopt an upwardly directed configuration in relation to the plane of the liquid-permeable covering. The side flaps, which consist of both the covering layers of the product, have also been provided with various types of pretensioned elastic system which, when contracted, are drawn together and then also contract the side flaps which thus also adopt an upwardly directed configuration which provides a good barrier function. The advantage of this solution is that bodily fluids which run on top of the liquid-permeable surface layer have to pass two barriers before leakage occurs. The problems of this double-barrier solution are not principally associated with leakage prevention but rather with material cost, manufacture and comfort.

Double elasticated barrier systems mean that, before everything else, the costs of the elastic materials rise dramatically. Costs incurred for special types of fixing adhesive for fixing the elastic materials, which are often difficult to fix, also increase if use is made of double elastic systems. Fixing elastic systems using adhesive is currently the most common fixing method and, because fixing elastic materials is complicated, extremely expensive adhesive qualities in great quantities must in most cases be selected. Moreover, extra elastic materials and adhesive mean that the environment-friendliness of the absorbent article is impaired.

As far as the manufacture of absorbent articles is concerned, which has to take place at high rates in order to achieve satisfactory profitability, each new material component of the absorbent article also means that the number of process steps in the manufacturing process increases, which in turn means that the number of places in the manufacturing machine where there is a risk of machine stoppage occurring increases. Starting up/restarting a more complex manufacturing machine which is to manufacture an article containing a number of starting materials is also more difficult and more time-consuming than starting up a simpler machine for manufacturing a less complex article containing fewer material components. The number of substandard products which lack one or some material components also increases with a larger number of component materials, and these products have to be rejected, which reduces the profitable use of raw materials. Furthermore, a larger number of material components of elastic type, which are normally supplied to the production machine in roll form, means more roll changes, which requires a higher manning level for production in the machine with maximum effectiveness. New material components which are added to the absorbent article also mean, as mentioned above, that the manufacturing machine becomes more complex, with increased maintenance costs as a result.

Elastic components applied in association with projecting free edges on the absorbent product, such as on the free edge of the inner barrier or on the outermost edge of the side flap, are moreover unfortunate from the point of view of comfort because the free edge is both folded and stiffened, with an increased tendency to chafe as a result. The elastic system itself and the extra adhesive which is normally required for anchoring the elastic system result in a considerable increase in the stiffness of the elasticated edge, which often causes the wearer irritation problems. The irritation problems are particularly great because the purpose of the elastic is, by means of its elastic capacity, to press against the thigh sides or against the groins of the wearer so as to provide sealing.

DISCLOSURE OF INVENTION

The problem of providing an absorbent article with a double barrier system without having to use more elastic material than is required for absorbent articles with only a single barrier system is solved by the present invention.

The present invention also solves the problems of the high material costs which conventional absorbent articles with a double barrier system involve.

Moreover, the present invention provides an absorbent article with a double barrier system which can be manufactured on a production machine without the extra elastic-application units which are conventionally required for manufacturing absorbent articles with a double barrier system.

Discomfort such as chafing caused by the stiffness of hard elasticated edges is also reduced considerably with the present invention because the absorbent article does not contain as many stiff elasticated edges.

A product of the type referred to in the introduction made according to the invention is characterized mainly in that each liquid barrier is, at least in the crotch portion of the product, in the region between its attachment to the absorbent product and its free edge, fixed to the adjacent side flap outside the edges of the absorbent body, as a result of which the product has double raised leakage barriers arranged along the edges extending in the longitudinal direction.

By means of the invention, it is therefore possible to bring about a double edge barrier, only one of the barriers being elasticated, at least in the crotch portion of the product. In this connection, either the inner barriers or the outermost side flaps are elasticated.

In a product according to the invention, the elasticated barrier element brings the unelasticated barrier element with it into an upwardly directed configuration when the elasticated barrier element is contracted and is brought into an upwardly directed configuration.

According to a preferred embodiment, the inner barrier is elasticated and fixed to the unelasticated side flap located outside.

According to another embodiment, the outer side flap is elasticated and fixed to the unelasticated barrier located inside.

According to a further embodiment, both the inner barrier and the side flap lying outside comprise the same material.

According to a further embodiment, the side flap comprises parts of the liquid-permeable covering layer.

According to a further embodiment, both the inner barrier and the side flap lying outside comprise parts of the liquid-permeable covering material.

BRIEF DESCRIPTION OF DRAWINGS

The invention will be described in greater detail below with reference to the exemplary embodiments shown in the appended figures, in which.

DESCRIPTION OF EMBODIMENTS OF THE INVENTION

The invention relates to an absorbent product such as a nappy, an incontinence pad, a sanitary towel or the like.

Figure 1:
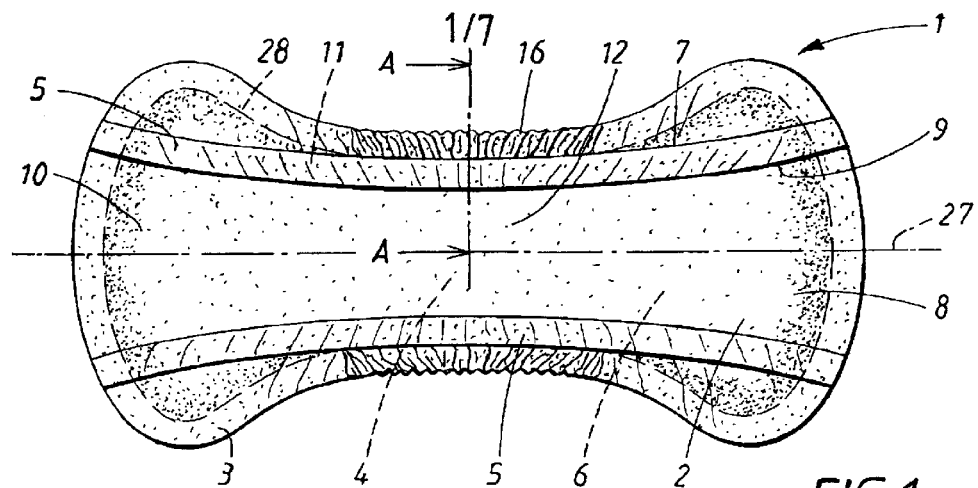
FIG. 1 shows an absorbent product seen from the side which is intended to face the wearer during use.
Figure 2:
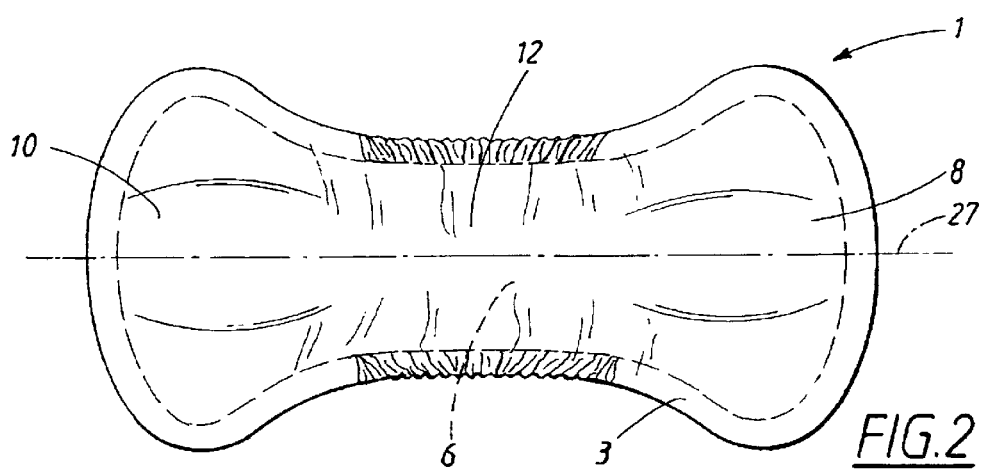
FIG. 2 shows an absorbent product seen from the side which is intended to face away from the wearer during use.

The embodiment shown in FIGS. 1 and 2 relates to an incontinence pad 1 for milder forms of incontinence. The incontinence pad 1 is hourglass-shaped and in this connection has two wider end portions 8 and 10, and a narrower crotch portion 12 located between the end portions 8 and 10. The crotch portion 12 is intended to be located, during use, in the narrowest region between the thighs of the wearer and is the region of the incontinence pad 1 which, during normal use, is wetted first by discharged bodily fluid.

The incontinence pad 1 comprises a first, liquid-permeable covering layer 2, arranged over that surface of the incontinence pad 1 which is intended to face the wearer during use, a second, liquid-impermeable covering layer 4 arranged over that surface of the product which is intended to face away from the wearer during use, an absorption body 6 enclosed between the two covering layers 2 and 4, side flaps 3 arranged outside the absorption body 6, inner barriers 5 arranged in association with the side flaps 3 on that side of the incontinence pad 1 which is intended to face the wearer during use.

The liquid-permeable covering layer 2 extends beyond the absorption body 6 along the entire circumference of the absorption body 6. The liquid-permeable covering layer 2 can consist of any material suitable for the purpose. Examples of commonly used liquid-permeable covering materials are non-woven textile materials, perforated plastic films, net made of plastic or textile, and liquid-permeable foam layers. Liquid-permeable covering materials which consist of continuous thin fibres extending essentially in the longitudinal or transverse direction of the product are also found. Laminates consisting of two or more of the above-mentioned possible covering materials are also common, as are coverings consisting of different materials in different parts of the surface.

The liquid-impermeable covering layer 4 extends beyond the absorption body 6 along the entire circumference of the absorption body 6. The liquid-impermeable covering layer 4 can also consist of a number of different materials. Most commonly, the liquid-impermeable covering layer 4 consists of a thin liquidtight plastic film, but it is also possible to use other types of liquidtight material, such as non-woven materials which have been made liquidtight by, for example, coating with plastic, liquidtight foam layers, liquidtight adhesive or the like. The liquid-impermeable covering layer 4 can also consist of a vapour-permeable material.

Absorbent products of the type described usually also comprise a fastening system for fixing the product to the underwear of the wearer. Such a fastening system usually comprises one or more adhesive strands arranged on the liquid-impermeable covering layer 4 of the absorbent product and a protective layer arranged over the adhesive strands. Other types of fastening system are also possible, for example layers of high-friction material, layers of touch-and-close material or the like. No fastening system is shown in the figures.

The covering layers 2 and 4 are interconnected outside the absorption body 6 along the entire circumference of the absorption body 6. The covering layers 2, 4 can be interconnected in a great many different ways. Examples of methods of connection are gluing, hot-melting, ultrasonic welding or the like.

The absorption body 6 can consist of one or more layers of cellulose fluff pulp. The cellulose fluff pulp can in this connection be mixed with fibres or particles of a highly absorbent polymeric material of the type which during absorption chemically binds great quantities of liquid while forming a liquid-containing gel. The absorption body 6 can also include additional components for improving the properties of the absorption body 6. Examples of such components are binding fibres, various types of liquid-spreading layers or fibres, shape-stabilizing components, reinforcing fibres or the like. The absorption body 6 can of course also consist of other types of absorption material, such as absorbent non-woven materials, absorbent foam, textile materials, peat, or mixtures of different types of absorption material. Special layers for rapidly receiving larger quantities of liquid and temporarily storing this liquid, and subsequently passing the temporarily stored liquid on to other parts of the absorption body 6, can also form part of the absorption body.

The inner barriers 5 extend in the longitudinal direction essentially parallel to the longitudinal symmetry line 27 of the incontinence pad 1, at least in the crotch portion 12 of the incontinence pad 1. The inner barriers 5 are arranged essentially symmetrically in relation to the longitudinal symmetry line 27 of the incontinence pad 1. Each inner barrier 5 has an edge 9 attached to the liquid-permeable covering layer 2 and a free edge 7.

Each inner barrier 5 is connected to the adjacent side flap 3 at least in the crotch portion 12 of the incontinence pad 1.

The connection of the inner barrier 5 to the adjacent side flap 3 can be made in a number of ways. It can be a continuous linear connection, a number of shorter linear connections, a number of spot connections or a single spot connection preferably arranged in the crotch portion 12 of the product. Other geometrical connection methods or combinations of the connection methods described can also be used. Examples of connection types are gluing, fusion welding, ultrasonic welding, sewing or the like.

The inner barriers 5 comprise elastic elements 11 which have been connected to the inner barriers 5 in a pretensioned state. When the pretensioned elastic elements 11 are released, they contract together with the inner barriers 5 to which the elastic elements 11 have been connected. The inner barriers 5 are then brought into a raised configuration away from the liquid-permeable covering layer 2. In this connection, the inner barriers 5 also bring the side flaps 3 into a raised configuration away from the plane of the liquid-permeable covering layer 2 on account of the connection between the inner barriers 5 and the side flaps 3.

The elastic elements 11 are arranged between the free edges 7 of the inner barriers 5 and the attached edges 9 of the inner barriers 5. The elastic elements 11 can consist of, for example, one or more elastic threads, one or more elastic bands, strips of elastic plastic films, strips of elastic non-woven material, elastic foam material or the like. The elastic elements 11 can be connected to the inner barriers 5 in a number of different ways. Examples of connection methods are gluing, welding, sewing or the like.

Figure 1A:
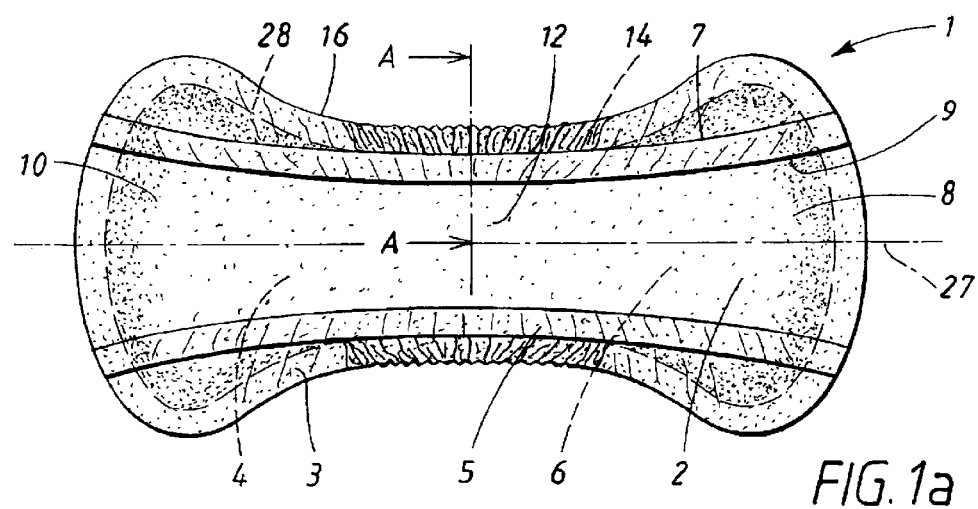
FIG. 1*a* shows an alternative embodiment of an absorbent product seen from the side which is intended to face the wearer during use.

The alternative embodiment shown in FIGS. 1a and 2 shows an incontinence pad 1 which corresponds to the incontinence pad according to FIGS. 1 and 2 apart from the fact that the incontinence pad 1 in FIGS. 1a and 2 does not comprise elastic elements connected to the inner barriers 5. Instead, elastic elements 14 are arranged in the side flaps 3.

The elastic elements 14 have been connected to the side flaps 3 in a pretensioned state. When the pretensioned elastic elements 14 are released, they contract together with the side flaps 3 to which the elastic elements 14 have been connected. The side flaps 3 are then brought into a raised configuration. In this connection, the side flaps 3 also bring the inner barriers into a raised configuration away from the plane of the liquid-permeable covering layer 2 on account of the connection between the inner barriers 5 and the side flaps 3.

The elastic elements 14 are arranged between the longitudinal edges 28 of the absorption body 6 and the free edges 16 of the side flaps. The elastic elements 14 can consist of the same type of elastic element as the elastic elements 11. The elastic elements 14 can be connected to the side flaps 3 in the same way as the elastic elements 11 can be connected to the inner barriers 5.

Figure 3:
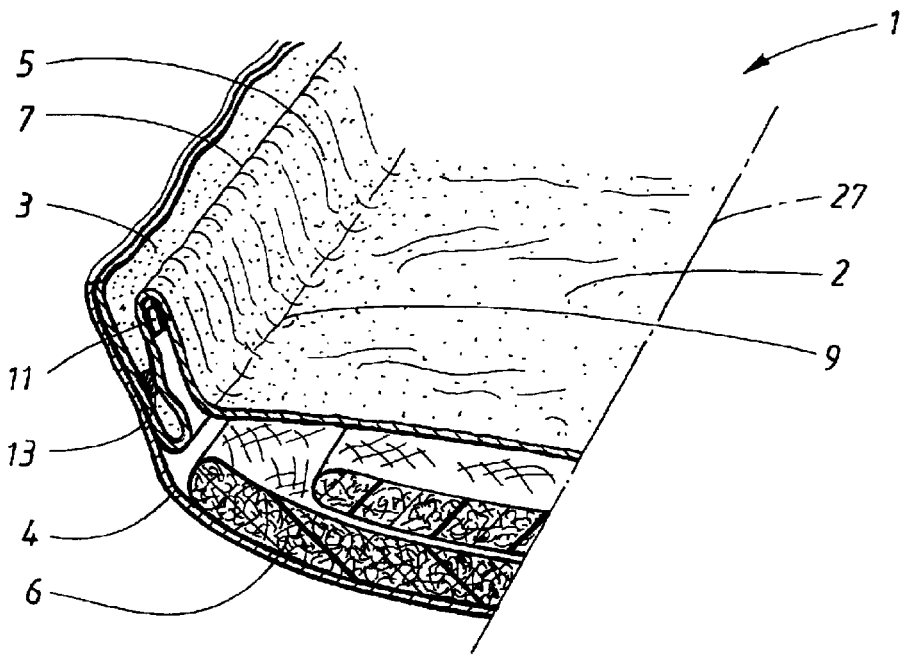
FIG. 3 shows a cross-sectional view through a barrier on the product in FIGS. 1 and 2 according to a first embodiment of the invention.
Figure 4:
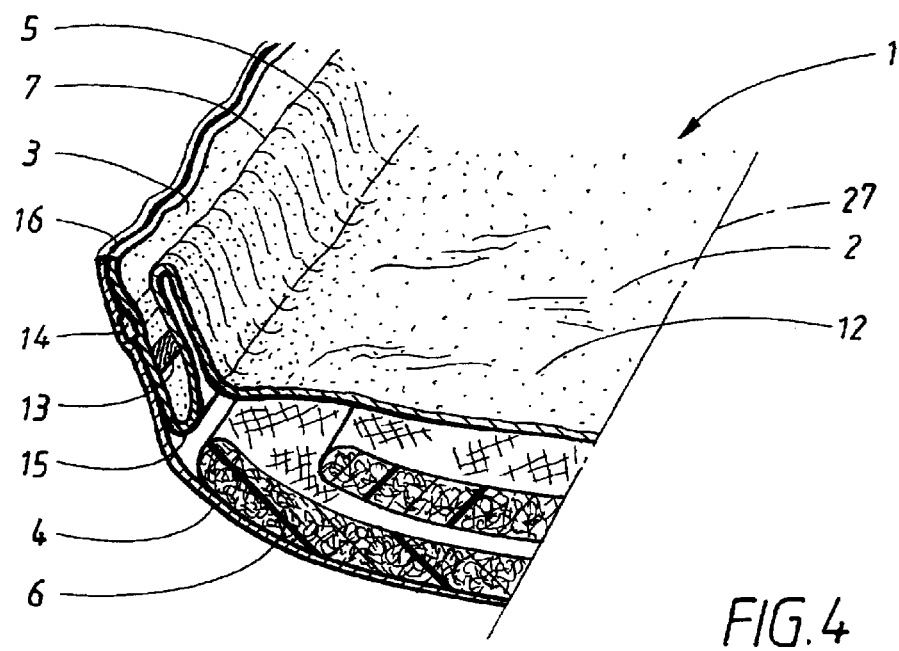
FIG. 4 shows a cross-sectional view through a barrier on the product in FIGS. 1*a* and 2 according to a second embodiment of the invention.

FIGS. 3 and 4 show enlarged cross sections of a part of an incontinence pad 1 through one inner barrier 5 and one side flap 3 of the incontinence pad 1 in the crotch portion 12. The cross-sectional view in FIG. 3 shows an embodiment of the incontinence pad 1 according to FIGS. 1 and 2, while the cross-sectional view in FIG. 4 shows an embodiment of the incontinence pad 1 according to FIGS. 1a and 2.

The projecting side flap 3 comprises the two covering layers 2, 4 which are interconnected by adhesive.

The projecting inner barrier 5 is arranged on that side of the liquid-permeable covering layer 2 which is intended to face the wearer, and projects from the plane of the covering layer. The inner barrier 5 is formed by a fold in the liquid-permeable covering layer 2. The inner barrier 5, which therefore consists of the same material as the liquid-permeable covering material 2, can be made less liquid-permeable by, for example, hydrophobing. In this connection, only that part of the initially liquid-permeable material which constitutes the inner barrier 5 is hydrophobed. Hydrophobing can be brought about in a great many different ways, for example by spraying hydrophobing agent onto the material, or transferring hydrophobing agent from a transfer roller. The inner barrier 5 can also be made less liquid-permeable by laminating those parts of the initially liquid-permeable material which constitute the inner barrier 5 together with different types of less liquid-permeable material, such as thin strips of plastic film, hydrophobic non-woven strips or the like. It is also possible to elect to reduce the liquid-permeability of the inner barrier 5 in only a limited area of its longitudinal extent. In this case, the hydrophobing or lamination described is carried out only along part of parts of the longitudinal extent of the inner barrier 5, for example in only the crotch portion 12 of the incontinence pad 1.

The incontinence pad 1 in FIG. 3 has an elasticated inner barrier 5. The inner barrier 5 is connected to the side flap 3 by adhesive 13. The elastic element 11 applied in a pretensioned state, which is arranged in association with the free edge 7 of the inner barrier 5, is connected to the inner barrier 5, at least in the end portions of the elastic element. On contraction, the elastic element 11 brings both the inner barrier 5 and the side flap 3 into a raised configuration in the direction away from the plane of the liquid-permeable covering layer 2.

The contraction of the material in the inner barrier 5 increases from the fixed edge 9 of the inner barrier 5 to the outermost part of the elastic element 11, that is to say that part of the elastic element 11 which is located nearest to the free edge 7 of the inner barrier.

The incontinence pad 1 in FIG. 4 has an elasticated side flap 3. The side flap 3 is connected to the inner barrier 5 by adhesive 13. The elastic element 14 is arranged between the attached edge 15 of the side flap 3 and the free edge 16 of the side flap 3, preferably nearer to the free edge of the side flap 3 than to the attached edge 15 of the side flap 3. The elastic element 14 extends in the longitudinal direction of the incontinence pad 1. On contraction, the elastic element 14 brings both the inner barrier 5 and the side flap 3 into a raised configuration away from the plane of the liquid-permeable covering layer 2.

Figure 5:
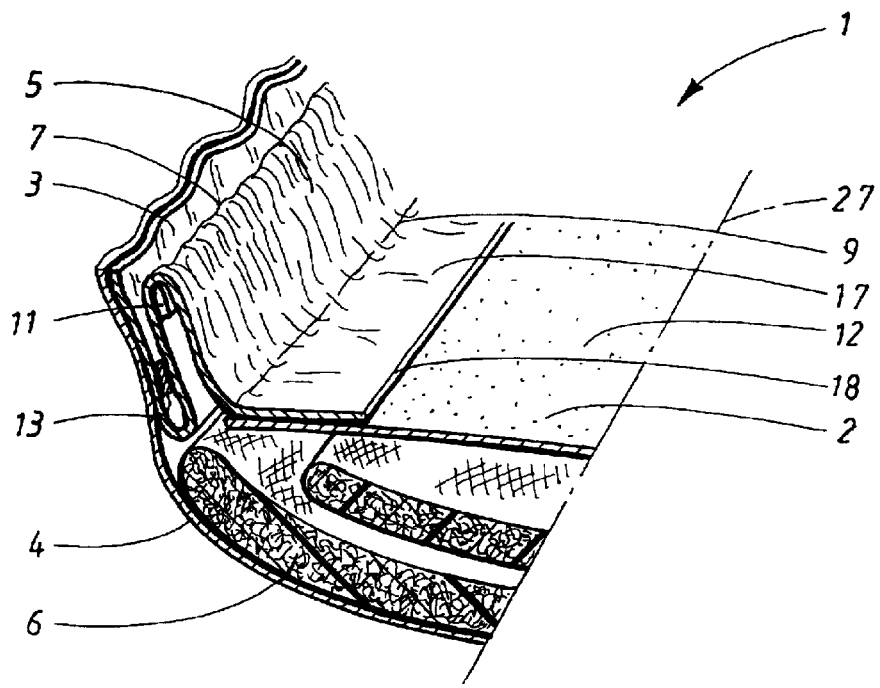
FIG. 5 shows a cross-sectional view through a barrier on the product in FIGS. 1 and 2 according to a third embodiment of the invention.
Figure 6:
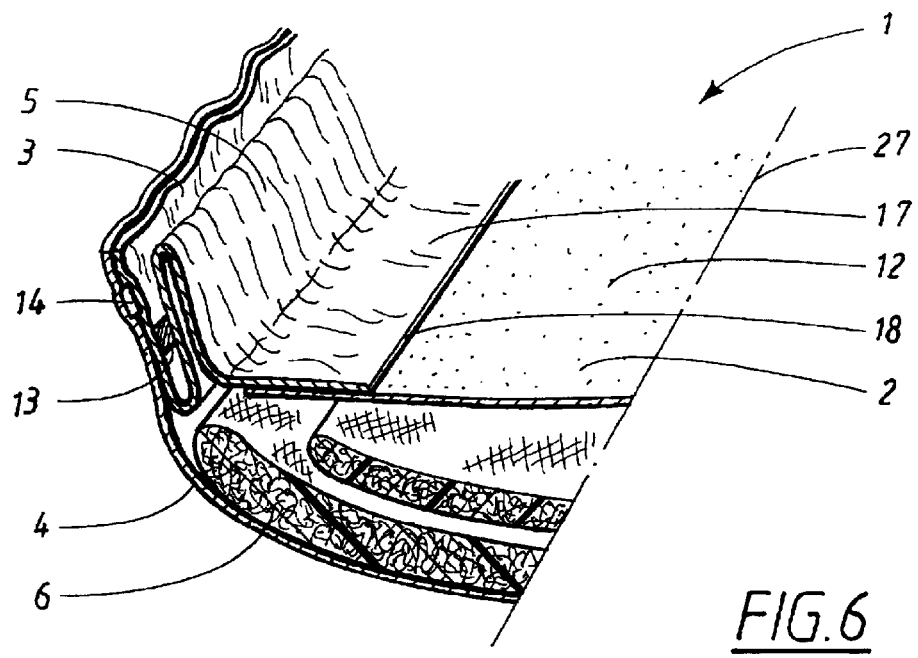
FIG. 6 shows a cross-sectional view through a barrier on the product in FIGS. 1*a* and 2 according to a fourth embodiment of the invention.

FIGS. 5 and 6 show enlarged cross-sectional views of an incontinence pad 1 through one inner barrier 5 and one side flap 3 of the incontinence pad 1 in the crotch portion 12. The projecting side flap 3 comprises the liquid-impermeable covering layer 4. The inner barrier 5 and the side flap 3 comprise an essentially liquid-impermeable material web 17. The material web 17 has an inner longitudinal edge 18 located between the inner barrier 5 and the longitudinal centre line 27 of the incontinence pad 1. The material web 17 is connected to the liquid-permeable covering layer 2 between the inner barrier 5 and the longitudinal centre line 27 of the incontinence pad 1. The liquid-impermeable covering layer 4 and the material web 17 are interconnected outside the absorption body 6.

Figure 7:
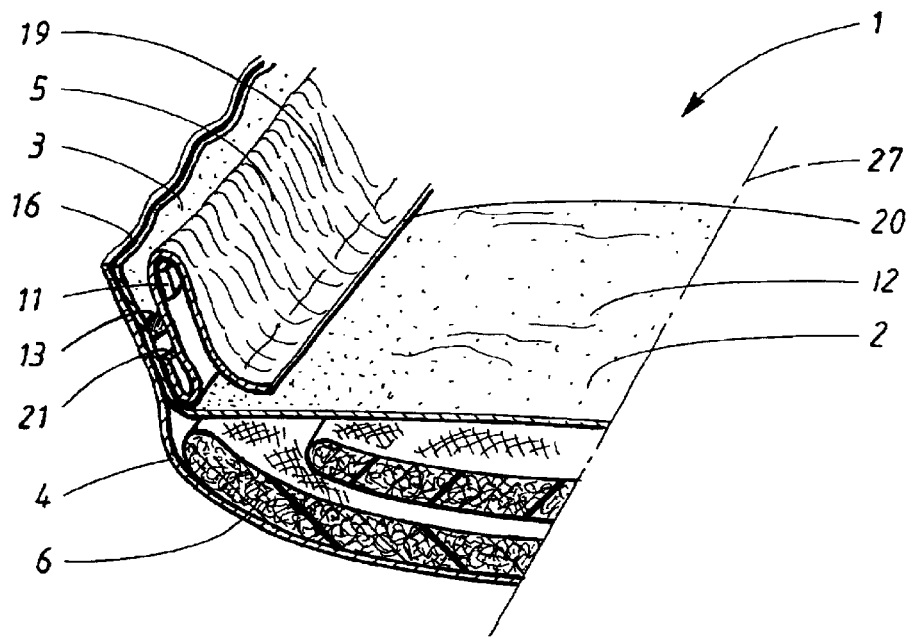
FIG. 7 shows a cross-sectional view through a barrier on the product in FIGS. 1 and 2 according to a fifth embodiment of the invention.
Figure 8:
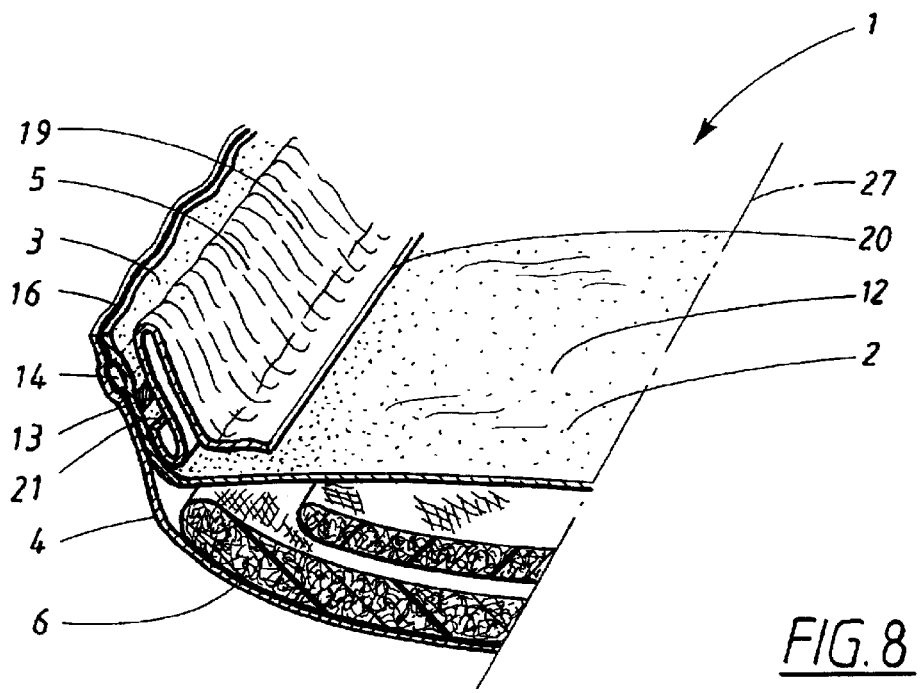
FIG. 8 shows a cross-sectional view through a barrier on the product in FIGS. 1*a* and 2 according to a sixth embodiment of the invention.

FIGS. 7 and 8 show enlarged cross-sectional views of an incontinence pad 1 through one inner barrier 5 and one side flap 3 of the incontinence pad 1 in the crotch portion 12. The cross-sectional view in FIG. 7 shows an embodiment of the incontinence pad 1 according to FIGS. 1 and 2, while the cross-sectional view in FIG. 8 shows an embodiment of the incontinence pad 1 according to FIGS. 1a and 2.

The projecting side flap 3 is formed by the liquid-impermeable covering layer 4 and the liquid-permeable covering layer 2.

The inner barrier 5 comprises an essentially liquid-impermeable material web 19. The material web 19 has an inner longitudinal edge 20 located between the inner barrier 5 and the longitudinal centre line 27 of the incontinence pad 1, and an outer longitudinal edge 21 located between the barrier 5 and the free edge 16 of the side flap 3. The material web 19 is connected to the liquid-permeable covering layer 2 between the inner barrier 5 and the longitudinal centre line 27 of the incontinence pad 1 and between the barrier and the free edge 16 of the side flap 3.

Figure 9:
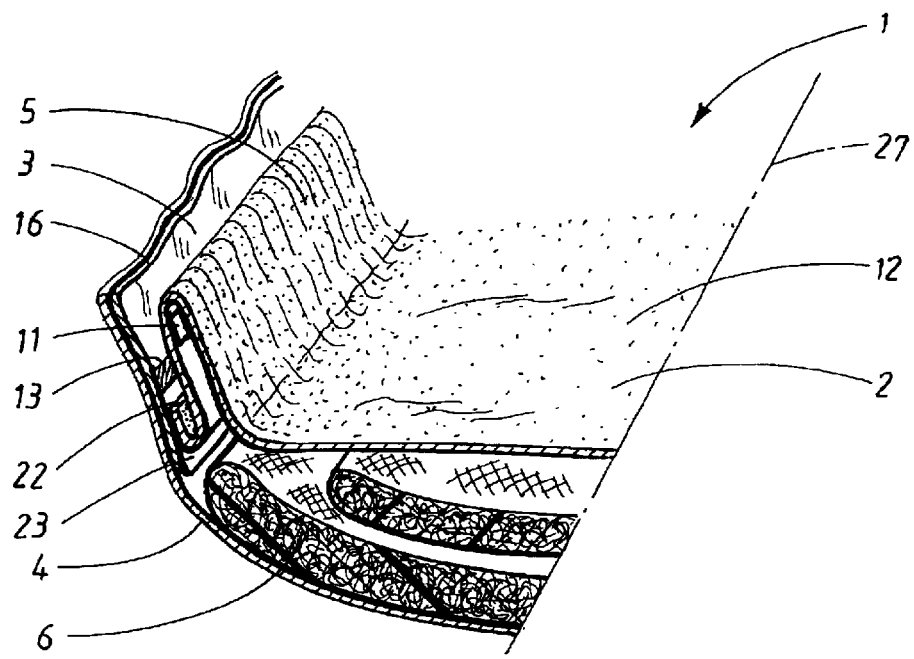
FIG. 9 shows a cross-sectional view through a barrier on the product in FIGS. 1 and 2 according to a seventh embodiment of the invention.
Figure 10:
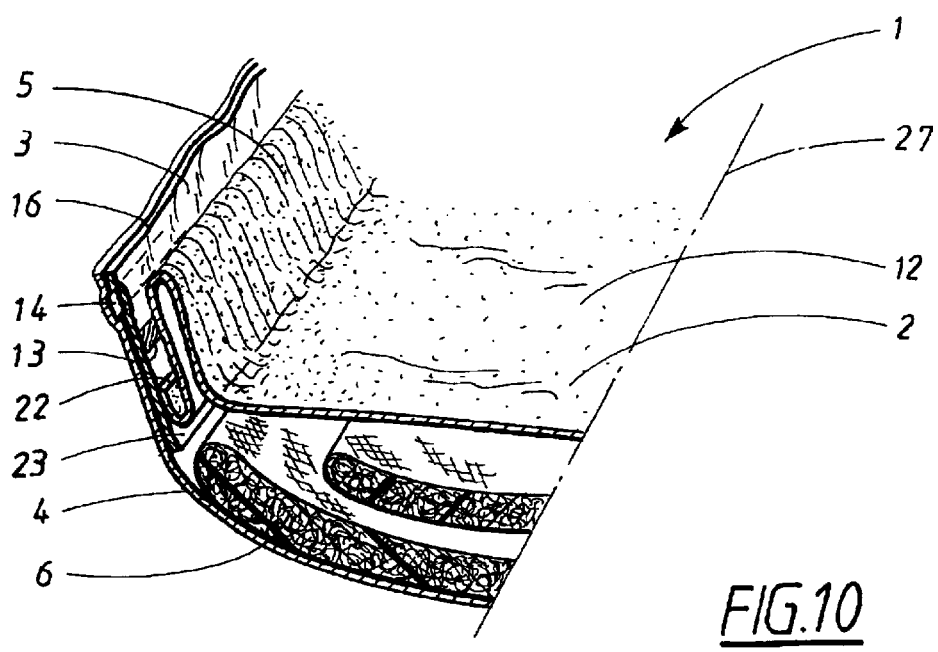
FIG. 10 shows a cross-sectional view through a barrier on the product in FIGS. 1*a* and 2 according to an eighth embodiment of the invention.

FIGS. 9 and 10 show enlarged cross-sectional views of an incontinence pad 1 through one inner barrier 5 and one side flap 3 of the incontinence pad 1 in the crotch portion 12. The inner barrier 5 is formed by the liquid-permeable covering layer 2.

The liquid-permeable covering layer 2 has an outer longitudinal edge 22 located between the barrier 5 and the free edge 16 of the side flap 3. The side flap 3 can comprise a soft, comfortable material web 23. The liquid-permeable covering layer 2 is connected to the side flap 3 between the barrier 5 and the free edge 16 of the side flap 3.

Figure 11:
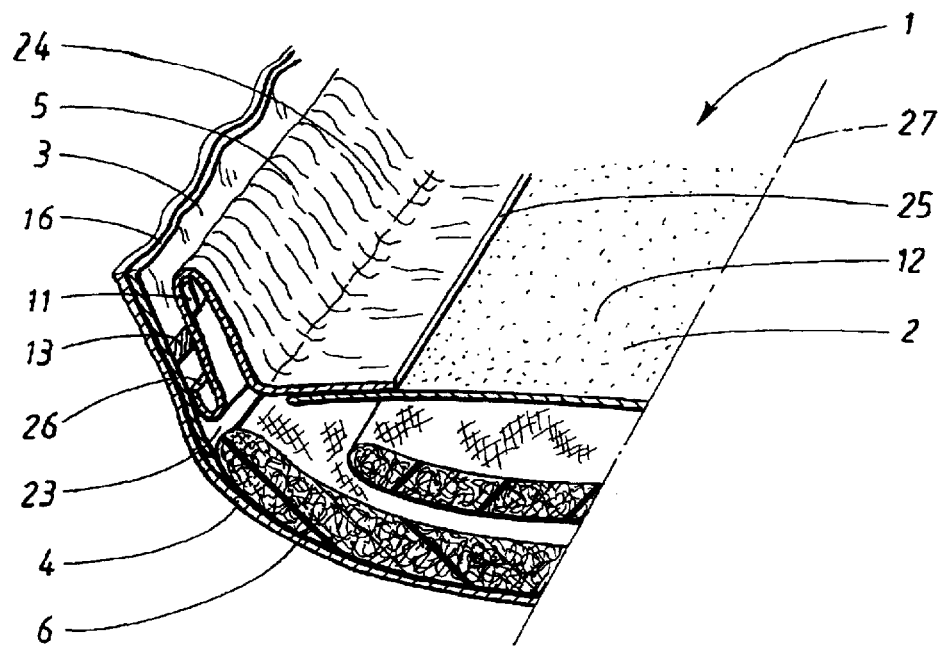
FIG. 11 shows a cross-sectional view through a barrier on the product in FIGS. 1 and 2 according to a ninth embodiment of the invention.
Figure 12:
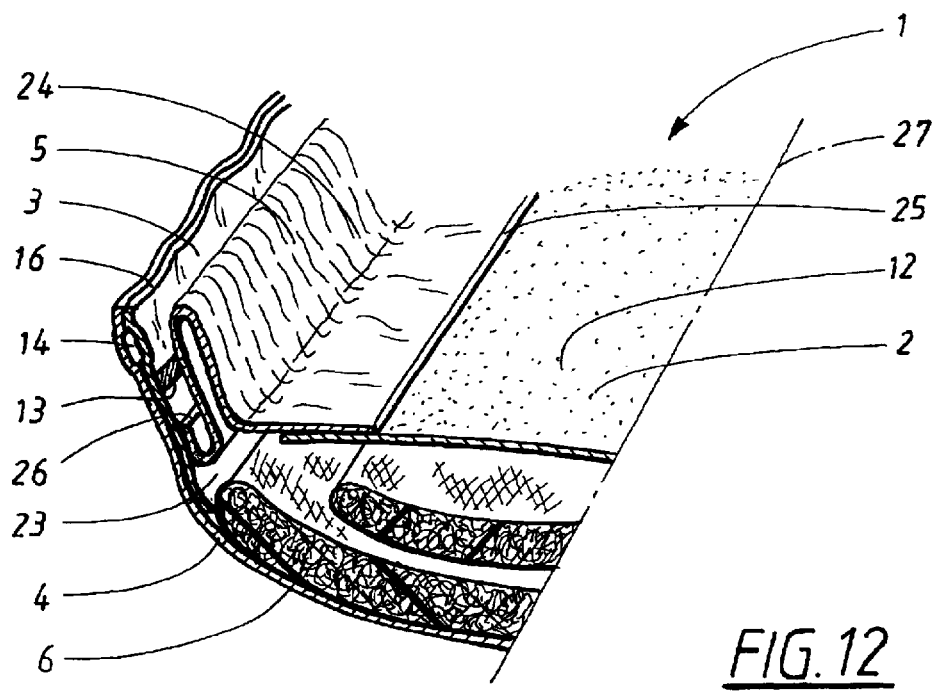
FIG. 12 shows a cross-sectional view through a barrier on the product in FIGS. 1*a* and 2 according to a tenth embodiment of the invention.

FIGS. 11 and 12 show enlarged cross-sectional views of an incontinence pad 1 through one inner barrier 5 and one side flap 3 of the incontinence pad 1 in the crotch portion 12. The inner barrier 5 comprises an essentially liquid-impermeable material web 24. The material web 24 has an inner longitudinal edge 25 located between the inner barrier 5 and the longitudinal centre line 27 of the absorbent product 1. The material web 24 is connected to the liquid-permeable covering layer 2 between the inner barrier 5 and the longitudinal centre line 27 of the product 1. The essentially liquid-impermeable material web 24 has an outer longitudinal edge 26 located between the inner barrier 5 and the free edge 16 of the side flap 3. The side flap 3 can comprise a soft, comfortable material web 23. The liquid-impermeable material web 24 is connected to the side flap 3 between the inner barrier 5 and the free edge 16 of the side flap 3.

Figure 13:
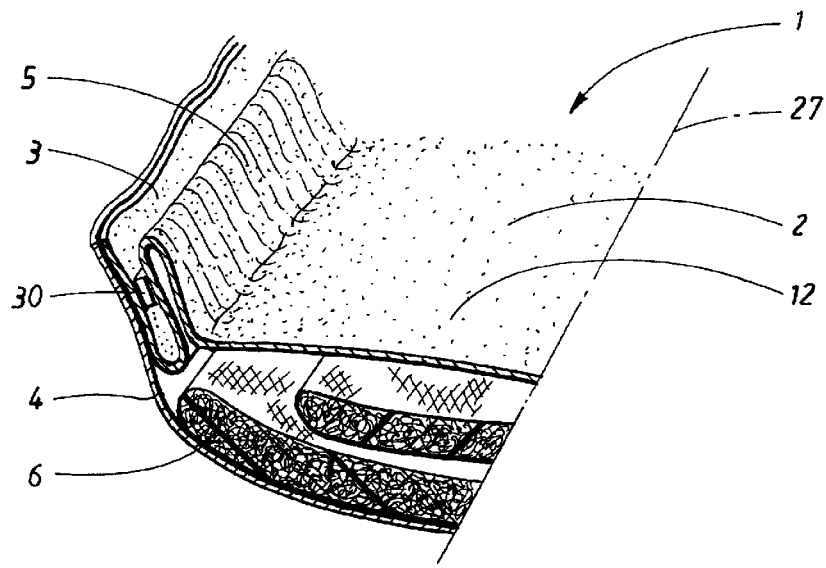
FIG. 13 shows a cross-sectional view through a barrier on the product according to an eleventh embodiment of the invention.

FIG. 13 shows an enlarged cross-sectional view of an incontinence pad 1 through one inner barrier 5 and one side flap 3 of the incontinence pad 1 in the crotch portion 12. The projecting side flap 3 is formed by the two covering layers 2, 4 which are interconnected by adhesive. The inner barrier 5 is formed by a fold in the liquid-permeable covering layer 2. The inner barrier 5 can be made less liquid-permeable in the same manner as the corresponding inner barrier 5 of the embodiments according to FIGS. 3 and 4. The inner barrier 5 and the side flap 3 are interconnected, at least in the crotch portion 12 of the incontinence pad 1.

The incontinence pad 1 according to FIG. 13 has an elastic element 30 applied in a pretensioned state arranged between the inner barrier 5 and the side flap 3. The elastic element 30 is suitably connected to both the inner barrier 5 and the side flap 3 at least in the end portions of the elastic element 30 and at least at a point between the end portions of the elastic element 30. On contraction, the elastic element 30 brings both the inner barrier 5 and the side flap 3 into a raised configuration away from the plane of the liquid-permeable covering layer 2.

Figure 14:
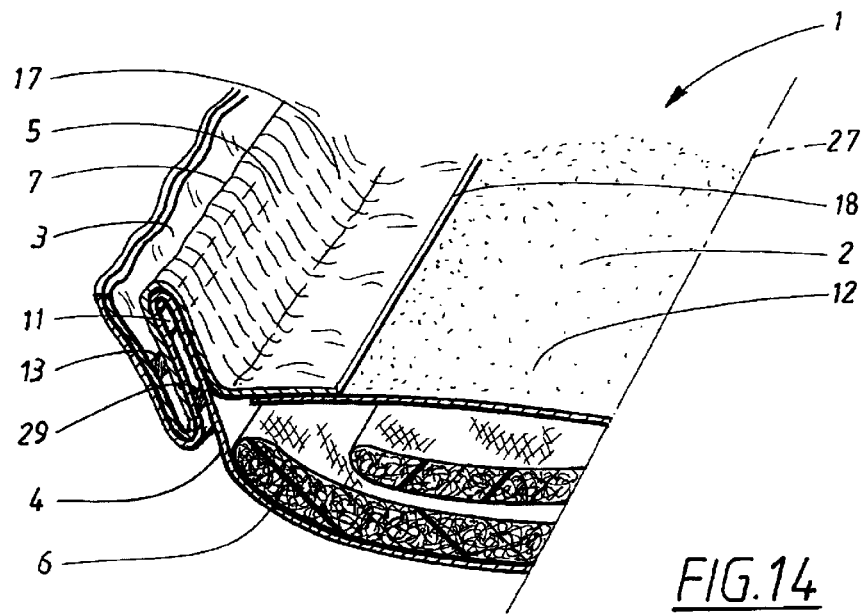
FIG. 14 shows a cross-sectional view through the product in FIG. 1 according to a twelfth embodiment of the invention.

FIG. 14 shows an enlarged cross-sectional view of an incontinence pad 1 through one inner barrier 5 and one side flap 3 of the incontinence pad 1 in the crotch portion 12. The inner barrier 5 and the side flap 3 comprise an essentially liquid-impermeable material web 17. The material web 17 has an inner longitudinal edge 18 located between the inner barrier 5 and the longitudinal centre line 27 of the incontinence pad 1. The material web 17 is connected to the liquid-permeable covering layer 2 between the inner barrier 5 and the longitudinal centre line 27 of the incontinence pad 1. The liquid-impermeable covering layer 4 and the material web 17 are interconnected outside the absorption body 6.

The inner barrier 5 is formed by a fold in the connected parts of the liquid-impermeable covering layer 4 and the material web 17, the fold being fixed in position by adhesive 29. The inner barrier 5 is connected to the side flap 3 by adhesive 13.

The incontinence pad 1 in FIG. 14 has an elasticated inner barrier 5. The inner barrier 5 is connected to the side flap 3 by adhesive 13. The elastic element 11 applied in a pretensioned state, which is arranged in association with the free edge 7 of the inner barrier 5, is connected to the inner barrier 5, at least in the end portions of the elastic element. On contraction, the elastic element 11 brings both the inner barrier 5 and the side flap 3 into a raised configuration in the direction away from the plane of the liquid-permeable covering layer 2.

What is claimed is:

1. Absorbent product having a longitudinal direction and a transverse direction and comprising:
   a front and a rear end portion,
   an intermediate crotch portion,
   edges extending in the longitudinal direction and in the transverse direction,
   an upper, liquid-permeable surface layer,
   a lower, liquid-impermeable surface layer,
   an absorbent body arranged between the surface layers and comprising edges in the longitudinal direction and in the transverse direction,
   liquid barriers extending in the longitudinal direction arranged essentially parallel to those edges of the product running in the longitudinal direction, the liquid barriers each having a free edge,
   side flaps extending in the longitudinal direction outside the liquid barriers and comprising parts of at least one of the surface layers, and
   elastic elements extending in the longitudinal direction and fastened to only the liquid barriers without an elastic element being connected to the side flaps, the liquid-permeable surface layer extending in the longitudinal direction of the product at least between the liquid barriers,
   wherein each liquid barrier is, at least in the crotch portion of the product, in a region between an attachment to the absorbent product and each said free edge, fixed to the adjacent side flap outside the edges of the absorbent body, as a result of which the product has double raised leakage barriers arranged along the edges extending in the longitudinal direction.

2. Absorbent product according to claim 1, wherein the elastic elements comprise one of: at least one elastic thread, at least one elastic band, at least one strip of elastic plastic film, at least one strip of elastic non-woven material and elastic foam material.

3. Absorbent product according to claim 1, the side flaps comprising liquid barrier material.

4. Absorbent product according to claim 1, wherein the side flaps comprise parts of the liquid-permeable surface layer.

5. Absorbent product according to claim 1, wherein both the side flaps and the liquid barriers comprise parts of the liquid-permeable surface layer.

6. Absorbent product according to claim 1, wherein both the liquid barriers and the side flaps comprise parts of the liquid-impermeable surface layer.

7. Absorbent product according to claim 1, wherein the side flaps comprise parts of the liquid-impermeable surface layer.

8. An absorbent product comprising:
   a liquid-permeable surface layer;
   a liquid-impermeable surface layer;
   an absorbent body between the liquid-permeable and liquid-impermeable surface layers and having edges extending in a longitudinal direction of the absorbent product, said liquid-permeable and liquid-impermeable surface layers and said absorbent body extending along an intermediate crotch portion between first and second end portions;
   liquid barriers extending in the longitudinal direction essentially parallel to said edges of said absorbent body, the liquid barriers each having a free edge;
   side flaps extending in the longitudinal direction outside the liquid barriers and comprising part of at least one of the liquid-permeable and liquidimpermeable surface layers; and
   elastic elements extending in the longitudinal direction and fastened to only the liquid barriers without an elastic element being connected to the side flaps,
   wherein each liquid barrier is fixed to an adjacent one of said side flaps in a region between said free edge and where said liquid barrier extends from said absorbent product, outside the edges of the absorbent body, so that the product has double raised leakage barriers arranged along the edges extending in the longitudinal direction.

9. The absorbent product according to claim 9, wherein the side flaps comprise part of the liquid-permeable surface layer.

10. The absorbent product according to claim 8, wherein the side flaps comprise part of the liquid-impermeable surface layer.

11. The absorbent product according to claim 8, wherein both the side flaps and the liquid barriers comprise part of the liquid-permeable surface layer.

12. The absorbent product according to claim 8, wherein both the liquid barriers and the side flaps comprise part of the liquid-impermeable surface layer.

13. The absorbent product according to claim 8, wherein the liquid barriers comprise part of the liquid-permeable surface layer.

14. The absorbent product according to claim 8, wherein the liquid barriers comprise part of the liquid-impermeable surface layer.

15. The absorbent product according to claim 8, wherein the side flaps comprise part of the liquid-permeable surface layer and part of the liquid-impermeable surface layer.

16. The absorbent product according to claim 8, wherein the elastic elements are only fastened to the liquid barriers.

* * * * *